United States Patent [19]

Keymling

[11] Patent Number: 5,009,639

[45] Date of Patent: Apr. 23, 1991

[54] GASTRIC/DUODENAL/JEJUNAL CATHETER FOR PERCUTANEOUS ENTERNAL FEEDING

[75] Inventor: Michael Keymling, Bad Hersfeld, Fed. Rep. of Germany

[73] Assignee: Fresenius, AG, Bad Homburg, Fed. Rep. of Germany

[21] Appl. No.: 184,628

[22] Filed: Apr. 22, 1988

[30] Foreign Application Priority Data

Apr. 23, 1987 [DE] Fed. Rep. of Germany ... 8705894[U]

[51] Int. Cl.[5] .......... A61M 25/00

[52] U.S. Cl. .......... 604/96; 604/178

[58] Field of Search .......... 604/96-103, 604/178

[56] References Cited

U.S. PATENT DOCUMENTS

| | | | |
|---|---|---|---|
| 2,677,375 | 5/1954 | Raiche | 604/96 |
| 2,936,761 | 5/1960 | Snyder | 604/96 |
| 3,144,868 | 8/1964 | Jascalevich | 604/96 |
| 3,640,282 | 2/1972 | Kamen et al. | 604/96 |
| 3,889,685 | 6/1975 | Miller, Jr. et al. | 128/344 |
| 3,971,385 | 7/1976 | Corbett | 604/96 |
| 4,344,434 | 8/1982 | Robertson | 604/334 |
| 4,356,824 | 11/1982 | Vazquez | 604/98 |
| 4,543,089 | 9/1985 | Moss | 604/96 |
| 4,601,713 | 7/1986 | Fuqua | 604/96 |
| 4,642,092 | 2/1987 | Moss | 604/96 |
| 4,658,812 | 4/1987 | Hatzewbuhler et al. | 604/96 |
| 4,685,901 | 8/1987 | Parks | 604/96 |
| 4,701,163 | 10/1987 | Parks | 604/178 |
| 4,795,430 | 1/1989 | Quinn et al. | 604/97 |

*Primary Examiner*—Stephen C. Pellegrino
*Assistant Examiner*—Ralph A. Lewis
*Attorney, Agent, or Firm*—Omri M. Behr

[57] ABSTRACT

A gastral/duodenal/jejunal catheter comprising a pair of catheter hoses, a balloon through which the hoses pass and a slidable disk, slidable around both of said hoses locatable between the balloon and the proximal ends of the hoses. The balloon, when inflated, is substantially ellipsoid in shape, having a short axis substantially coaxial with the longitudinal axis of the catheter hoses and is filled with an elastic compressible foam filling which is substantially collapsible upon extraction of air from the balloon.

4 Claims, 2 Drawing Sheets

GASTRIC/DUODENAL/JEJUNAL CATHETER FOR PERCUTANEOUS ENTERNAL FEEDING

FIELD OF THE INVENTION

The invention is concerned with a gastral/duodenal/-jejunal catheter for percutaneous entral feeding. It is particularly concerned with the percutaneous artificial feeding of patients directly into the stomach, duodenum or the jejunum.

DISCUSSION OF THE PRIOR ART

Catheters within the general concept of the present invention are disclosed in European Published Application 182 539. This application discloses a gastral or gastral/jejunal feeding probe which is insertable into the stomach wall of the patient through a stoma therein said probe being sealed against both sides of the abdominal wall. This probe or catheter may be used for the direct introduction of food into the stomach or into the jejunum.

As a further variant, a jejunal catheter is described which permits jejunal feeding by its direct placement into the jejunum.

In the described feeding probe, in the embodiment for gastral application, there is provided an inflatable balloon near the distal end thereof which insures that the probe does not slip out of the stomach. At the portion of the device which is not inserted into the abdomen, there is provided a moveable sealing ring which may be pressed against the outer surface of the patient's abdominal wall to insure that the probe does not slip further into the stomach. The balloon of the known device is completely collapsible and thus does not increase the circumference of the catheter by any noticeable amount. After introduction of the catheter from the outside through the stoma into the stomach, a air provision arrangement is attached to a connection piece therefore at the proximal end of the catheter and air is lead through an additional hose, which is part of the catheter, whose distal end opens internally in the said balloon. Thus, the balloon is inflated and closes the stoma from the inside. The disadvantage of this solution is that the substantially spherical form of the balloon does not provide a satisfactory contact surface with the stomach wall and thus, cannot provide an unequivocal protection against leakage. Furthermore, a substantially spherical balloon utilizes a relatively large volume. Thus, while the corresponding balloon catheter can be used without any disadvantage from this source in the substantially roomy stomach, it cannot be placed in the comparatively narrow thin intestine without a comparatively substantial consumption of room.

The aforesaid European published application provides yet another embodiment, specifically for positioning the device in the jejunum. In this embodiment, there is provided a jejunal catheter which is fixed in the stoma by means of a small synthetic ring. While this solution avoids the consumption of space within the thin intestine, it unfortunately offers less protection against leakage and against the accidental removal of the catheter. It would therefore be desirable to provide a gastral/-duodenal/jejunal catheter for the percutaneous entral feeding of patients which combines a low consumption of internal space with good assurance against leakage.

SUMMARY OF THE INVENTION

The invention is directed to a gastral/duodenal/jejunal catheter for percutaneous enteral having a channel for the delivery of a feeding solution and a second hose having a channel for the provision of a filling medium to a balloon and a balloon through which said first and second hoses pass. Said junction between said balloon and said hoses being sealed to be impervious to gas and liquid, the balloon being located proximal to the distal ends of said hoses. The second hose has an opening into the inside of said balloon close to its distal end. The balloon, when inflated, is substantially ellipsoid in shape.

In the preferred embodiment of the invention, there is further provided an elastic, compressible, similarly substantially ellipsoidal foam capsule within said ellipsoidal balloon. In this embodiment, a connection device is provided to the proximal end of second hose. An evacuation means, suitably a syringe, is attached to said connection means whereby the expansion component (suitably air) of the foam material may be removed. The thus provided reduced pressure permits the collapse of the balloon housing and of the flexible foam material which then lies against the surface of the catheter. Thus, also in this embodiment, the effective circumference of the catheter is negligibly increased.

After the catheter is introduced percutaneously into the stomach or the thin intestine, the aforesaid second hose is opened through the expansion forces of the compressed foam material. Air is sucked through said air hose whereby the foam body and therewith the balloon housing is expanded back into its normal shape. The ellipsoidal form of the foam body and of the balloon brings about a substantial amount of saving in room, particularly in the thin intestine and equally provides a sufficiently large contact surface to insure a sealing of the stomach and intestinal walls against leakage.

These embodiments of the invention avoid the problems which arise in the gastral or gastral jejunal probe disclosed in the prior art European application cited above.

The aforesaid prior art solution is subject to the further disadvantage that the balloon housing may tear and thus collapse, either during introduction thereof, or during its expansion or during the feeding process, whereby the catheter is no longer insured against accidentally slipping out of the abdominal cavity. In contrast thereto, the foam body in the balloon provided in accordance with the present invention, provides further protection against dislocation of the catheter since such accidental collapse of the balloon is not possible.

DETAILED DESCRIPTION OF THE DRAWINGS

Figure 1:
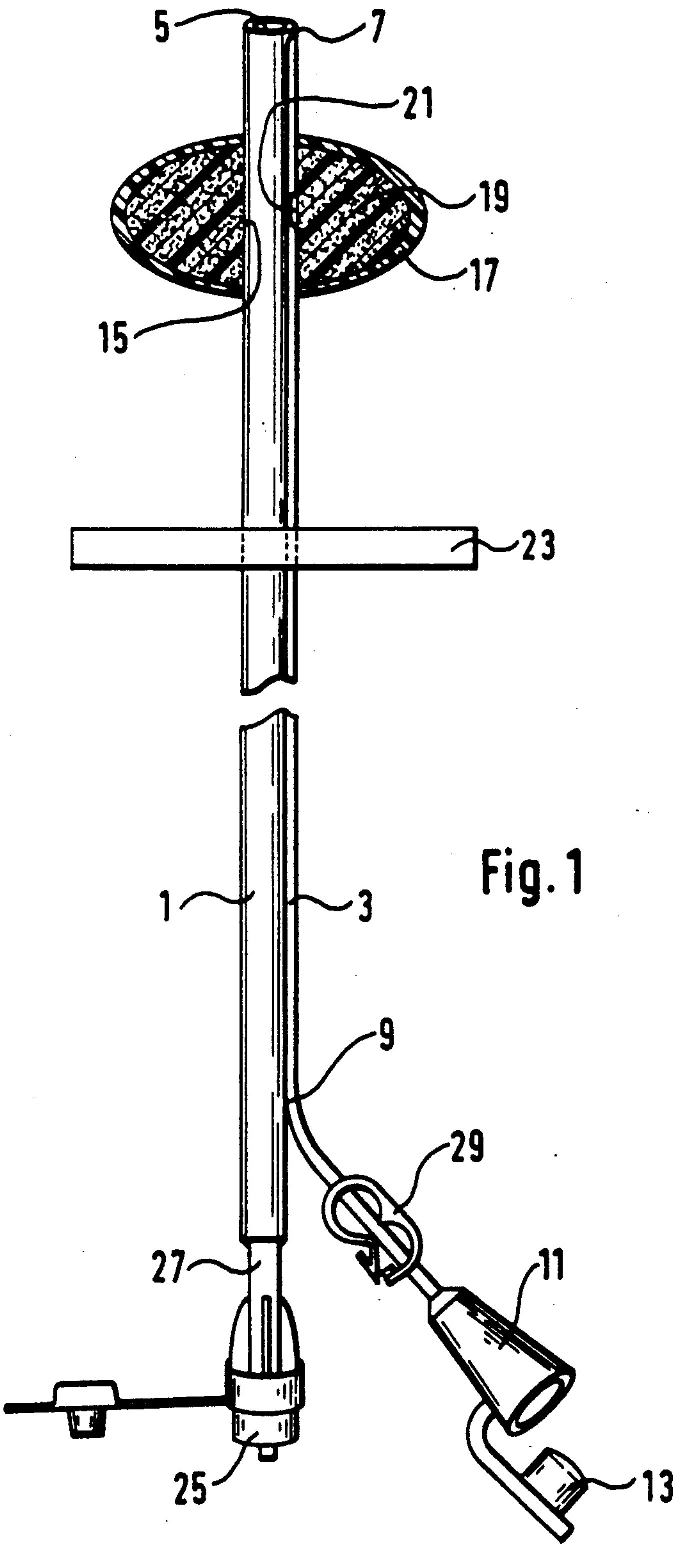
FIG. 1 is a cross-sectional view of the catheter of the present invention in its preferred embodiment, wherein the balloon comprises the foam material.

The catheter comprises a flexible catheter hose 1 further comprising in or on the wall thereof a separate similarly flexible hose formed air channel 3. Air channel 3 comprises a further opening 5 close to the sealed distal end 7 thereof. Channel 3 is separated from channel 1 at location 9 and is provided at its proximal end with a connection means 11, which may, if desired, be in the form of a Luer lock connector, a funnel connector or similar connector having an airtight closing means 13 attached between separating point 9 and connecting means 11. Near the distal end 5 of catheter hose 1, at location 15, there is provided a balloon 17 filled with a collapsible foam to provide the balloon 17 in substantially ellipsoidal form, with a short axis thereof, substantially coaxial with the longitudinal axis of hose 1. Said balloon 17 and the foam material therein are, as shown in FIG. 1, in normal circumstances, in ellipsoidal form. The junction between hoses 1 and 3 and balloon 17 is provided to be impermeable to gas and liquid.

An opening 21 is located close to the distal end 7 of air pipe 3 within the volume of balloon 17. Surrounding the hoses 1 and 3 of the catheter on the proximal side of balloon 17, is located slidable disk 23, which is locatable on the outside of the abdominal wall of the prospective patient. At the proximal end 27 of hose 1, there is provided a Luer lock connection 25 to which the hose or the container for synthetic feeding materials, may be connected. In the normal configuration, balloon 17 and the foam materials 19 therein are in the ellipsoidal form. Closing cap 13 may be opened and a one-way syringe is attached to connecting portion 11, said syringe is sized to have a volume substantially equal to or somewhat larger than the internal expanded volume of balloon 17. This syringe is utilized to extract the air (or other filling fluid) from inside balloon 17 and the foam material 19 therein. The clamp 29 is then closed, the syringe removed from connection portion 11 and the closure device 13 closed in an airtight manner.

In view of the underpressure of balloon 17, the foam material 19 and the balloon 17 are totally collapsed and provide an effective diameter negliglibly greater than the diameter of the combined hoses 3 and 1 at location 15. The catheter can thus be introduced through the abdominal wall into the stomach or thin intestine of the patient in When the catheter is located in the desired position, the closure cap 13 is removed from the connecting means 11, clamp 29 opened. The expansion forces within the foam body 19 cause the inhalation of air through tube 3 and the reorientation of the foam body and with it the balloon, into its original ellipsoidal shape. The expansion of the foam material 19 causes the surface of balloon 17 to lay itself against the stomach wall. The ellipsoidal structure of the foam material and with it the balloon 17 ensure that no unnecessary room is taken up inside the organs. Furthermore, the catheter is thus located in its desired position inside the body of the patient.

The disk 23 is now pushed onto the outside of the abdominal wall of the patient, thus ensuring that the catheter does not accidentally slip into the stomach or the thin intestine. The desired enteral feeding may now proceed through the luer lock connector 25 at proximal end 27 of hose 1. In order to achieve this, the catheter hose 1 is connected via a further hose (not illustrated) which passes through a peristaltic pump and whose further end is connected to a container for the feeding material.

The foam material is made from any of many readily available solid (as opposed to a liquid) but flexible cell wall materials. Among there may be mentioned synthetic rubbers, silicones, polyvinyl chloride, polystyrene, and the like. The cell size and air/solid (v/v) ratios of the foam material is not critical, provided the twin criteria of substantial collapsibility under reduced pressure and ready re-expansion at atmospheric pressure are met. Suitably however, the cell size is between 0.1 and 0.5 mm. in diameter and the air/solid (v/v) ratio is between 3:1 and 5:1.

Figure 2:
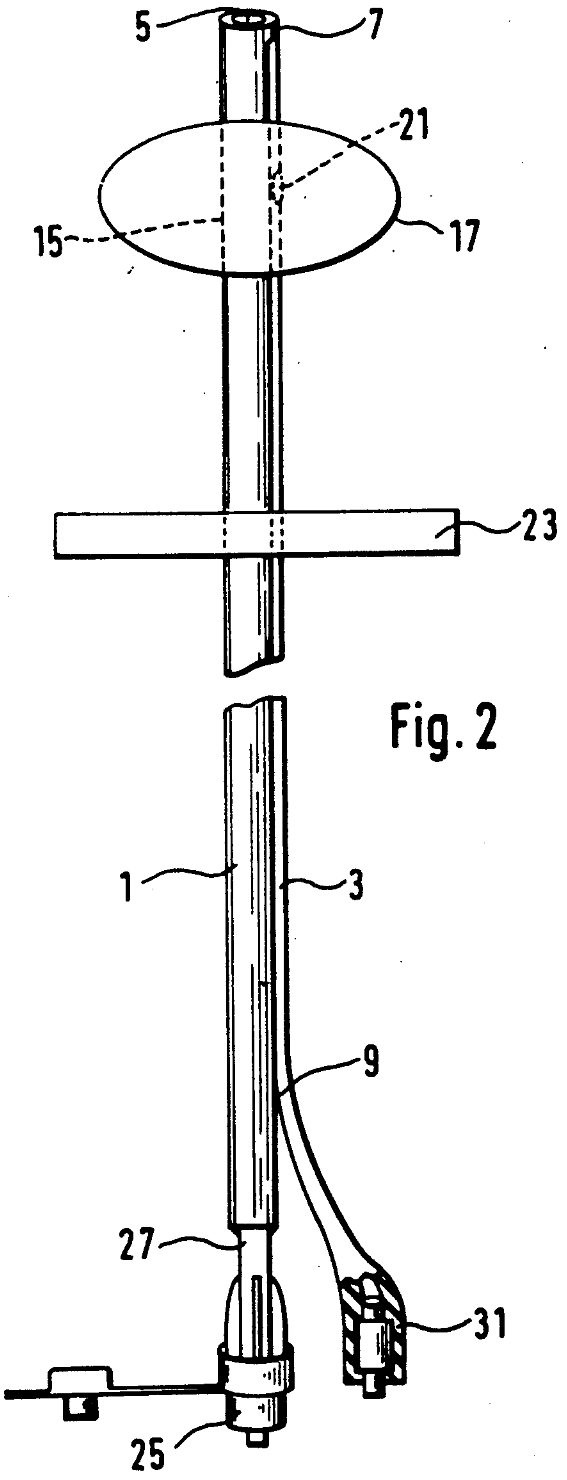
FIG. 2 is a cross-sectional view of the catheter of the present invention wherein the balloon does not contain the foam material.

FIG. 2 illustrates a further embodiment of the contain the foam filling. Upon deflation of the balloon, the balloon will, as in the previously discussed embodiment, lie against the catheter hose 1 in such a way that there is a negligible increase in the effective diameter of said hose 1. After the catheter is introduced through the abdominal wall into the stomach or the thin intestine in the usual manner, balloon 1 is then charged with a filling medium such as air or another fluid to its previously defined volume. This may be achieved by means of a syringe connected to balloon 17 via valve 31 attached to the proximal end of channel 3. This valve 31 prevents the accidental expulsion of the filling medium from balloon 17. It is the particular advantage of this invention that balloon 17 is particularly saving of space when inserted in the thin intestine and similarly, because of its large surface area, enables a good seal to be established at the stomach or intestinal wall.

We claim:

1. In a gastral/duodenal/jejunal catheter for percutaneous enteral feeding comprising:

a first catheter hose having a first channel for the delivery of a feeding solution, a second hose having a channel for the provision of a filling medium, both said hoses having proximal inflow and distal outflow ends, a balloon through which said first and second hose pass, wherein the junction between said balloon and said hoses is sealed to be impervious to gas and liquid, said balloon being located close to the distal end of said first hose and the distal end of said second hose being sealed but having an opening into the inside of said balloon, the improvement comprising (a) providing said balloon, when inflated, to be substantially ellipsoid in shape a short axis of said ellipsoid substantially coaxial with the longitudinal axis of said first catheter hose, said balloon being filled with an elastic, compressible, substantially ellipsoidal foam filling, said foam filling being substantially collapsible upon the extraction of air from the balloon, (b) further comprising a slidable disc, surrounding and slidable on said first and said second hoses locatable between said balloon and said proximal ends.

2. A catheter in accordance with claim 1, characterized thereby that the foam material is selected from the group consisting of polystyrene, polyvinyl chloride, silicones and synthetic rubber.

3. A catheter in accordance with claim 1, wherein said foam material when expanded has an air to solid ratio of from about 3:1 to about 5:1 (v/v).

4. A catheter in accordance with claim 1, wherein said foam material has a cell size from between 0.1 to 0.5 mm. in diameter.

* * * * *